(12) United States Patent
Lively et al.

(10) Patent No.: US 9,901,414 B2
(45) Date of Patent: Feb. 27, 2018

(54) ILLUMINATION SYSTEM WITH MAGNETIC MOUNT FOR LOUPES

(71) Applicants: Den-Mat Holdings, LLC, Lompoc, CA (US); Falcon Development B.V., Alkmaar (NL); Petrus Jacobus Keirsgieter, Alkmaar (NL)

(72) Inventors: Brenton Lively, Buelton, CA (US); Daniel Joseph Bodenstein, Boulder, CA (US); Brad Landtbom, Santa Maria, CA (US); Petrus Jacobus Keirsgieter, Heemskerk (NL); Maarten Jan Willem Toering, Wiljk Bij Duurstede (NL); Skylar Urban, Solvang, CA (US); Ryan Michael Welsh, Boulder, CO (US); Meg Tidd, Arvada, CO (US)

(*) Notice: Subject to any disclaimer, the term of this patent is extended or adjusted under 35 U.S.C. 154(b) by 140 days.

(21) Appl. No.: 14/791,064

(22) Filed: Jul. 2, 2015

(65) Prior Publication Data

US 2016/0076747 A1    Mar. 17, 2016

Related U.S. Application Data

(60) Provisional application No. 62/020,522, filed on Jul. 3, 2014, provisional application No. 62/090,046, filed on Dec. 10, 2014.

(51) Int. Cl.
*A61B 1/00* (2006.01)
*A61B 90/00* (2016.01)
(Continued)

(52) U.S. Cl.
CPC ........ *A61B 90/361* (2016.02); *A61B 1/00158* (2013.01); *A61B 1/06* (2013.01);
(Continued)

(58) Field of Classification Search
CPC ........ A61B 90/361; A61B 2017/00734; A61B 2090/309; A61B 2090/502;
(Continued)

(56) References Cited

U.S. PATENT DOCUMENTS 7,281,826 B2 * 10/2007 Huang ................. F21V 21/084
362/106
2012/0120636 A1    5/2012 Wilt et al.
(Continued)

FOREIGN PATENT DOCUMENTS

EM    001394225    12/2013

OTHER PUBLICATIONS

Orascoptic, "XV1 Loupe + Light", www.orascoptic.com/products/loupes/xv1-loupe-light, retrieved Oct. 2, 2015, USA.
(Continued)

*Primary Examiner* — Stephen F Husar
(74) *Attorney, Agent, or Firm* — Frederick W. Tong

(57) ABSTRACT

A headlamp magnetically mounted on a magnifying loupe for use in cosmetic, dental, medical, surgical, hobby and any other fields where an individual would find the ability to simultaneously illuminate and magnify a small area to be advantageous. The headlamp would contain an internal power source, so that there is no longer a need for a cable to connect the headlamp with the bulky external power source that is found in traditional loupe mounted headlamps.

14 Claims, 20 Drawing Sheets

(51) Int. Cl.
  *F21V 21/096* (2006.01)
  *F21V 21/084* (2006.01)
  *A61B 1/06* (2006.01)
  *G02B 25/00* (2006.01)
  *G02B 25/02* (2006.01)
  *A61B 17/00* (2006.01)
  *A61B 90/30* (2016.01)
  *A61B 90/50* (2016.01)

(52) U.S. Cl.
  CPC .......... *F21V 21/084* (2013.01); *F21V 21/096* (2013.01); *G02B 25/004* (2013.01); *G02B 25/02* (2013.01); *A61B 2017/00734* (2013.01); *A61B 2090/309* (2016.02); *A61B 2090/3616* (2016.02); *A61B 2090/502* (2016.02)

(58) Field of Classification Search
  CPC .............. A61B 2090/3616; A61B 1/06; A61B 1/00158; F21V 21/084; F21V 21/096; G02B 25/02; G02B 25/004
  USPC ........................................................ 315/158
  See application file for complete search history.

(56) References Cited

U.S. PATENT DOCUMENTS

2013/0094217 A1    4/2013  Nguyen
2013/0204094 A1*  8/2013  Fiebel .................. A61B 1/0692
                                          600/249

OTHER PUBLICATIONS

Falcon Development BV, "Binoc Falcon", www.binocfalcon.com/default.asp, retrieved Oct. 2, 2015, Netherlands.

* cited by examiner

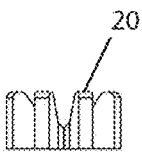
Fig. 30a
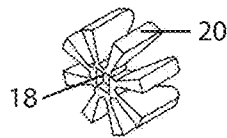
Fig. 30b
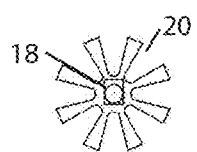
Fig. 30c
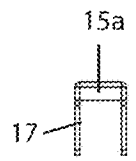
Fig. 31a
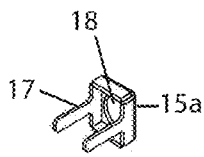
Fig. 31b
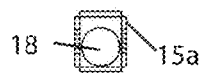
Fig. 31c
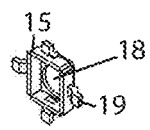
Fig. 32a
Fig. 32b
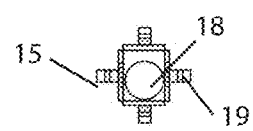
Fig. 32c
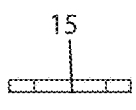
Fig. 33a
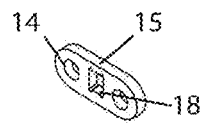
Fig. 33b
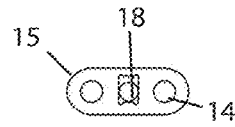
Fig. 33c

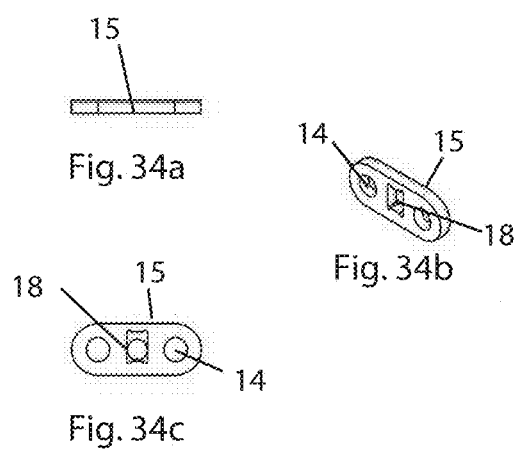

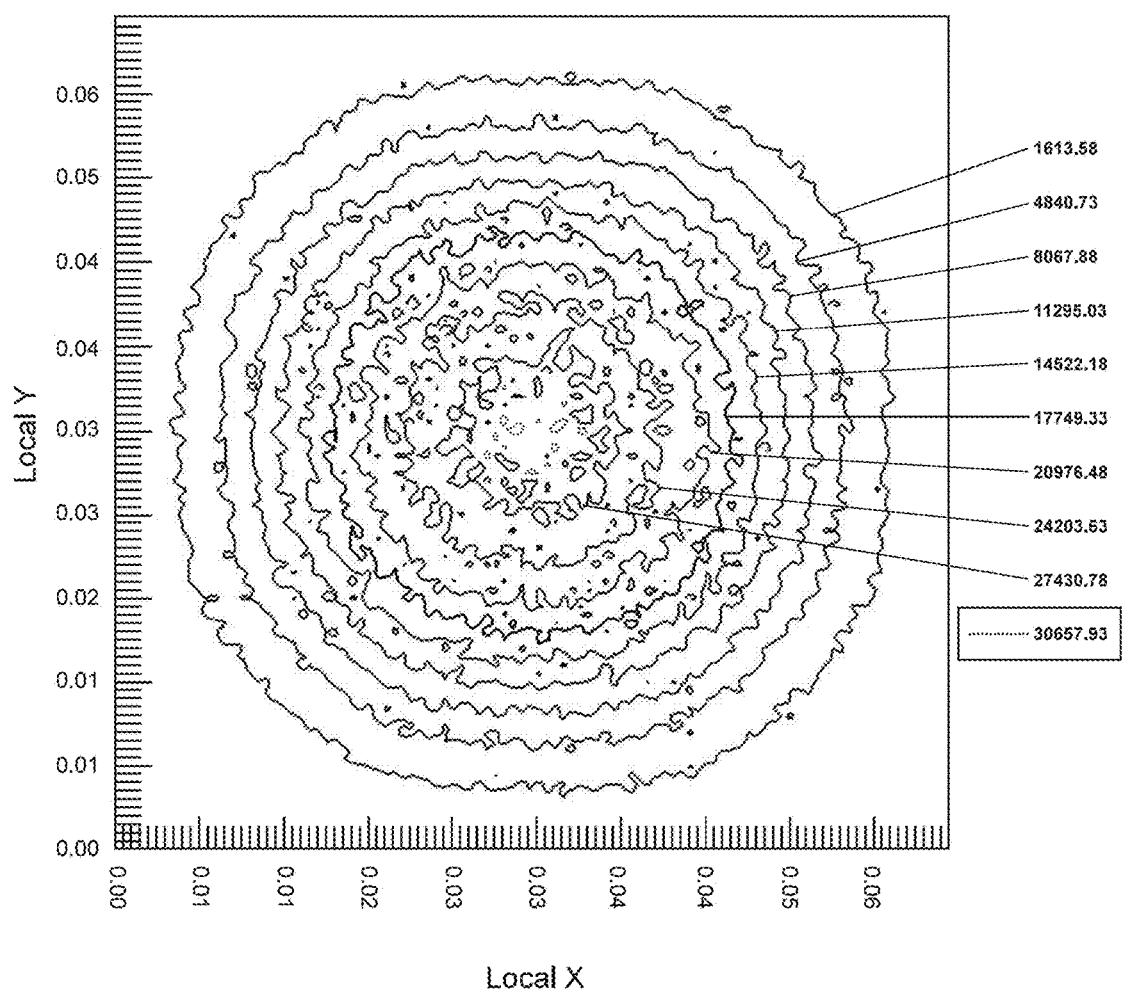

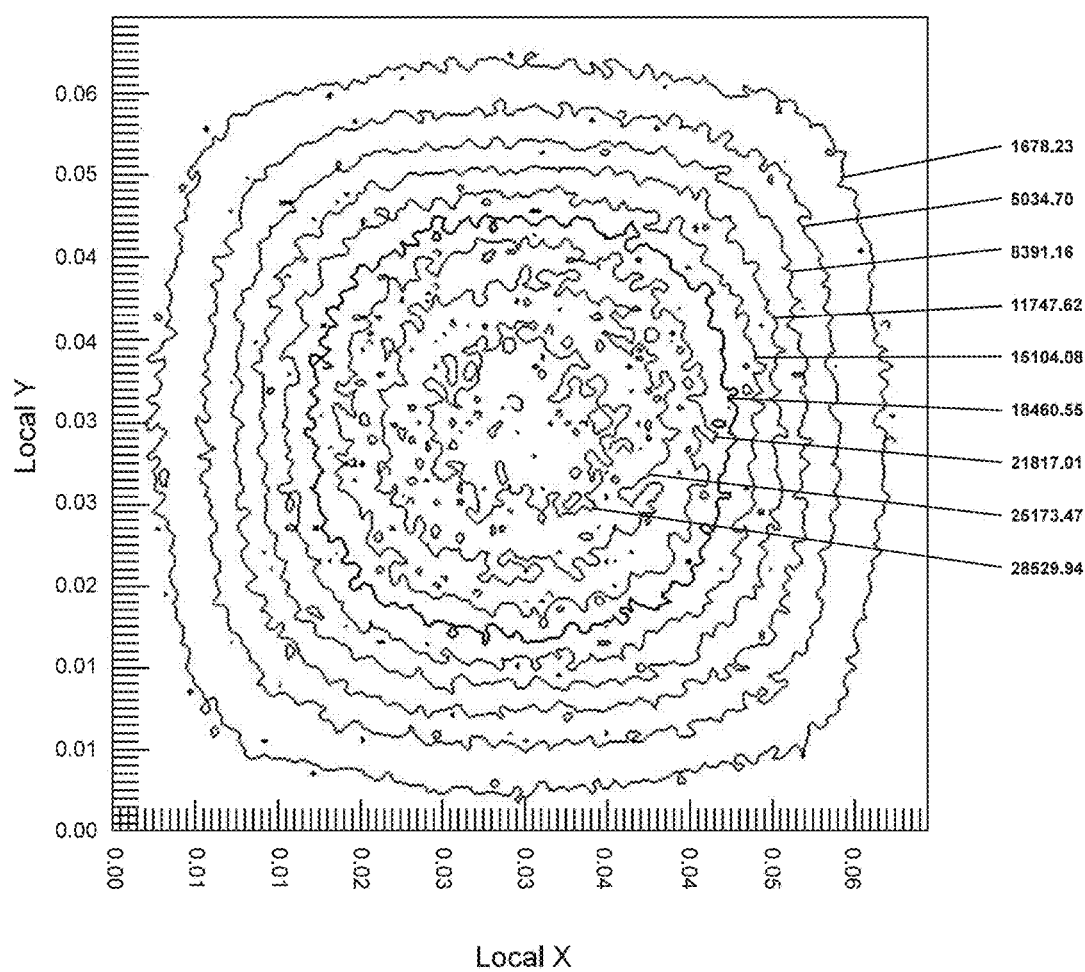

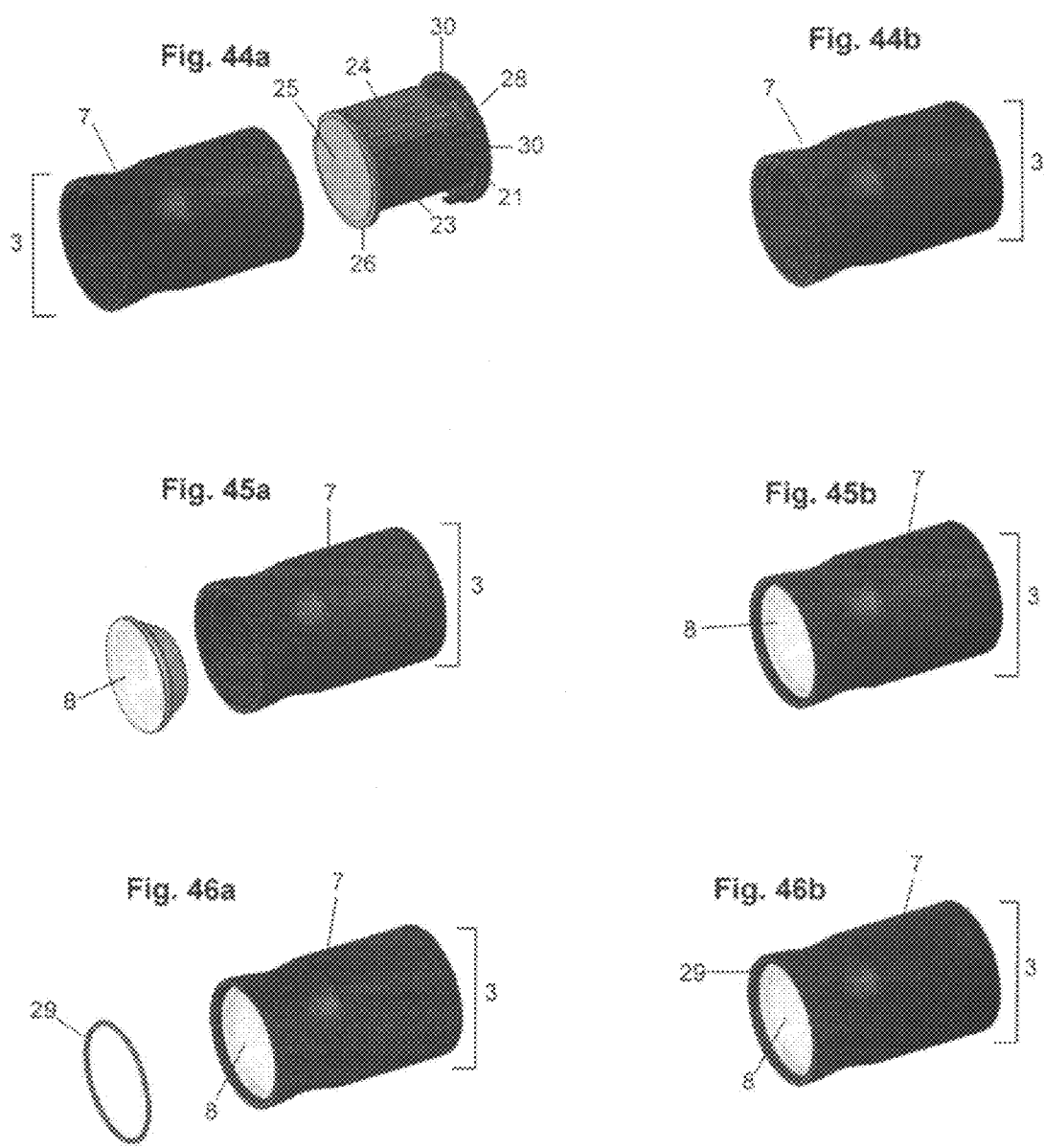

ILLUMINATION SYSTEM WITH MAGNETIC MOUNT FOR LOUPES

BACKGROUND OF THE INVENTION

Loupes are magnification devices that can improve dental, medical, or other treatments by magnifying small areas to aid an individual's ability to make fine and precise movements and actions. Fields as diverse as dental, medical and even various hobbies, such as model building and stamp collecting, can benefit from the use of loupes. In the dental and medical fields, loupes aid in magnifying small treatment areas in which the health practitioner seeks to make fine and precise movements and actions. An example would be a dentist using loupes to magnify a patient's oral cavity in order to find areas that require treatment, and being able to perform the fine movements required for treatment with enhanced precision. Another advantage to loupe usage is that by magnifying small areas, individuals may be able to work for extended times while enhancing the ability to practice better posture and ergonomics.

A headlamp used in conjunction with a loupe further enhances the advantages of loupe usage by directing light along the line of sight. By directing light in this manner, shadows that may be casted across the area being magnified can be eliminated.

Loups and accompanying headlamp technology is constantly changing. Loupes are becoming smaller and lighter. Similarly, headlamps have become more compact, lighter and brighter through the use of LEDs and other light sources. The power sources for these headlamps are similarly becoming more compact and lighter. Typically, the headlamp is mounted on the loupe frame or a headband and powered by a battery pack worn on the body and connected to the light with a cable.

Along with seeking to make headlamps more compact, lighter and brighter, there is also a growing demand to improve upon the output characteristics of LEDs and other lights sources. For example, creating a tighter spot of light that is projected on surface, more defined edges for the spot of light that is projected on a surface, improved collimation of the light and greater intensity. Traditional light output modifying means are often bulky, expensive and require high-precision fixtures and assemblies to accomplish their objectives. This is often at odds with the intended application and intent behind selecting a LED to begin with. The result is that there is a demand for a way to produce these improved LED output characteristics without these expensive high-precision fixtures and assemblies, and in a compact and low-cost fashion, more in-line with the objectives behind LED usage.

Additionally, there is always an interest in efficient heat dissipation and the resulting efficiency increases derived from maintaining a cooler junction temperature and longer run time of the LED.

Additionally, for dental, medical and surgical purposes, there is always interest in making headlamps easier to disinfect in the interest of safety for both the patient and the user. As medical and dental professionals are in contact with their patients, if they touch the headlamp to adjust the light, pathogens can be transferred to the headlamp. If the headlamp is not disinfected between procedures, pathogens can be transferred to new patients.

Thus, there is a need for lights with higher intensity, more compact size, lighter weight, more efficient lighting technologies, improved optics, improved cooling, less cabling to tether the operator and more compact power sources.

SUMMARY OF THE INVENTION

The preferred embodiment encompassed within the present invention is a headlamp to be used with a magnifying loupe for use in cosmetic, dental, medical, surgical, hobby and any other fields where an individual would find the ability to simultaneously illuminate and magnify a small area to be advantageous. Such a headlamp would contain an internal power source, so that there is no longer a need for a cable to connect the headlamp with the bulky external power source that is found in traditional loupe mounted headlamps.

Such a loupe and headlamp combination would contain the following elements: cordless light source powered with an internal battery; a mounting system for the headlamp that can be specific for the loupe frame, or be universally compatible with a wide range of loupe frames; the mounting system for the light can be available for both flip-up style loupes or through the lens (TTL) style loupes, as well as any other future loupe styles; and the mounting system or light should allow preferably for at least an angle of declination that would be usable by the individual wearing the system. One skilled in the art will recognize that the "battery" could include any means of powering a device. In addition, the entire system (housing, mount and charger) must be durable to survive the rigors of being handled all day long and have battery and product life that is at least comparable to current industry standard headlights.

The preferred LED incorporated in the light could incorporate a masking element to improve upon the characteristics of the light output and to better shape the light output. For example, medical and dental professions prefer having a circular shaped light as it provides for the same area of illumination regardless of orientation around said area or interest. In diagnostic efforts, it is important for the illumination source to be uniform and not draw a diagnostician's focus to one particular area being highlighted geometrically (such as the corner of a square for example). In non-diagnostic efforts, the opposite may be true where the device may be intended to draw extra focus to one particular area or feature. Using an LED mask presents a lighter, smaller and more cost effective way to shape the light.

Those skilled in the art will recognize that this description of the invention is not intending to be limited. Rather, there exists many possible changes, modifications and/or substitutions which can be made by one skilled in the art which does not depart from the spirit and scope of the invention.

BRIEF DESCRIPTION OF THE DRAWINGS

FIG. 30a is a side view of LED mask with integrated heat sink
FIG. 30b is an isometric view of LED mask with integrated heat sink
FIG. 30c is a top view of the LED mask with integrated heat sink
FIG. 31a is a side view of through-hole style LED mask
FIG. 31b is an isometric view of through-hole style LED mask
FIG. 31c is top view of through-hole style LED mask
FIG. 32a is a side view of the surface mount LED mask
FIG. 32b is an isometric view of the surface mount LED mask
FIG. 32c is a top view of the surface mount LED mask
FIG. 33a is a side view of the single block pocket style LED mask
FIG. 33b is an isometric view of the single block pocket style LED mask
FIG. 33c is top view of the single block pocket style LED mask
FIG. 34a is a side view of the multi-layer pocket style LED mask
FIG. 34b is an isometric view of the multi-layer pocket style LED mask
FIG. 34c is a top view of the multi-layer pocket style LED mask
FIG. 37 is an exit face contour plot
FIG. 38 is an exit face contour plot
FIG. 44a is an exploded view of the headlamp
FIG. 44b is an isometric view of the headlamp
FIG. 45a is an exploded view of the headlamp and lens
FIG. 45b is an isometric view of the headlamp mounted lens
FIG. 46a is an exploded view of the headlamp and O-ring
FIG. 46b is an isometric view of the headlamp mount O-ring

DETAILED DESCRIPTION OF THE INVENTION

The present invention is for a headlamp to be mounted on a frame commonly found in loupes used for medical, dental and hobby purposes. Such a headlamp would have the same light properties as traditional loupe mounted headlamps, but without the added bulk of a bulky external battery pack, and clutter created by the cabling between the bulk external battery pack and the headlamp.

Traditionally, medical and dental headlamps demanded a high level of luminance, which in turn required a lot of power. The only way to meet these power requirements was through a bulky and heavy external power pack. Because of the bulk and weight of these external power packs, they could not be located on the loupe frame itself, but rather, they had to be supported somewhere else, typically, worn around the waist and connected to the headlamp by a cord. The presence of the cord can be a hindrance to the user because it can be entangled with itself, the user, the instruments or furniture.

However, due to advances in battery and lighting technology, it is now possible to create a headlamp with the luminance properties of traditional headlamps, yet powered by internal batteries and doing away with the bulky external power packs. By removing the need for bulky external power pack, the headlamp would now be free of all external cabling. The benefits of a cordless headlamp include lighter weight of the device and all associated components, better weight distribution and fewer cords to entangle the user.

The weight of the system would be in the range of 10-200 g, with a preferred weight of approximately 20-40 g. The mount that connects the headlamp to the loupe frame is preferably articulated so that the location of the spot can be adjustable. For most standard medical and dental applications, the runtime would preferably be up to 960 minutes, so the headlamp could be used for a full day in an operatory. Although, operating within the limitations of current battery technology, a runtime of 60-90 minutes is desirable. Currently battery-charging technology has a charge time of 80% of the run time, however, it is anticipated that the charge time will decrease as battery and battery-charging technology improves.

A wide range of accessories would be available to customize the headlamp for use with particular applications. Such accessories would include different lights sources to change the spot shape, removable sleeves for cosmetic and/or asepsis purposes, light filters, extended life batteries, locking mechanisms, hinges, spot lights which can be indexed, clean spots, dimmers, carrying cases and travel cases.

Figure 1:
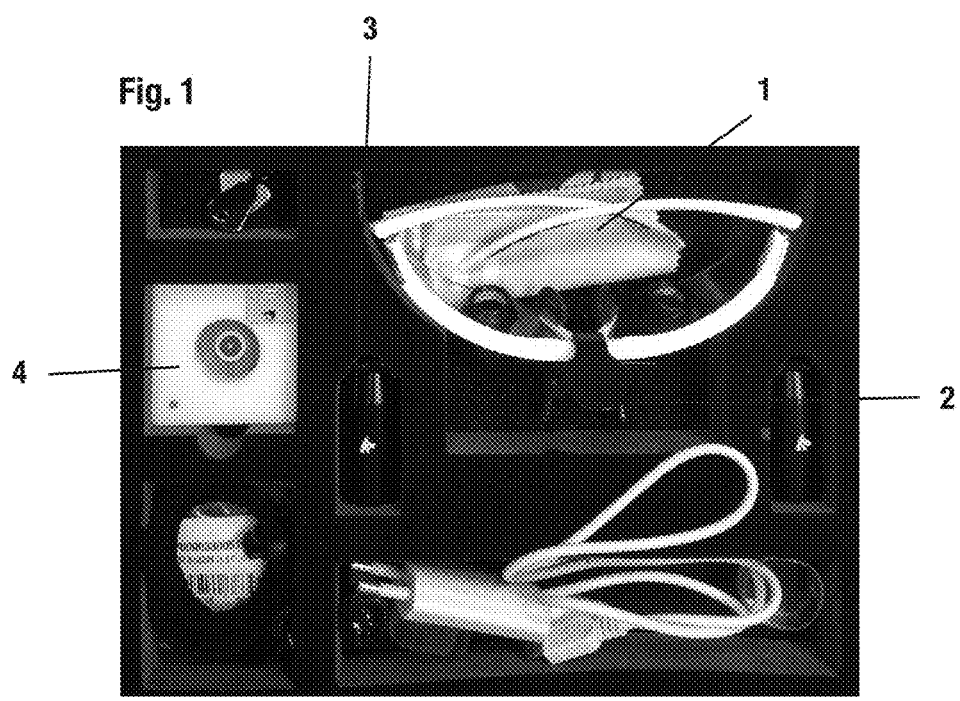
FIG. 1 is a top view of all the components

FIG. 1 depicts a kit containing all of the components that make up the present invention. These components include a frame 1 for mounting the headlamp on the user's head, a mount 2, at least one headlamp 3 and a charger 4. The frame 1 can simply be similar to an eyeglass frame, or it can be a more complex instrument, such as a through the lens (TTL) style pair of loupes.

Figure 2:
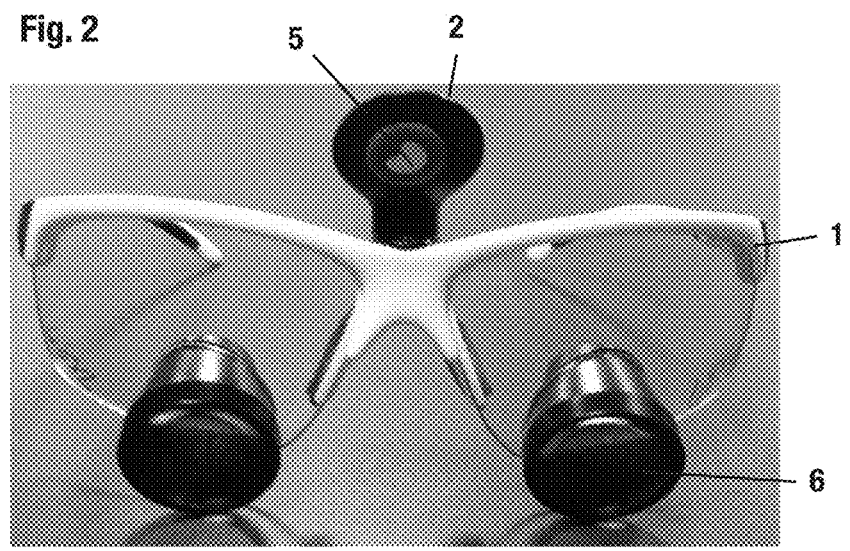
FIG. 2 is a front view of the loupe with the mount
Figure 3:
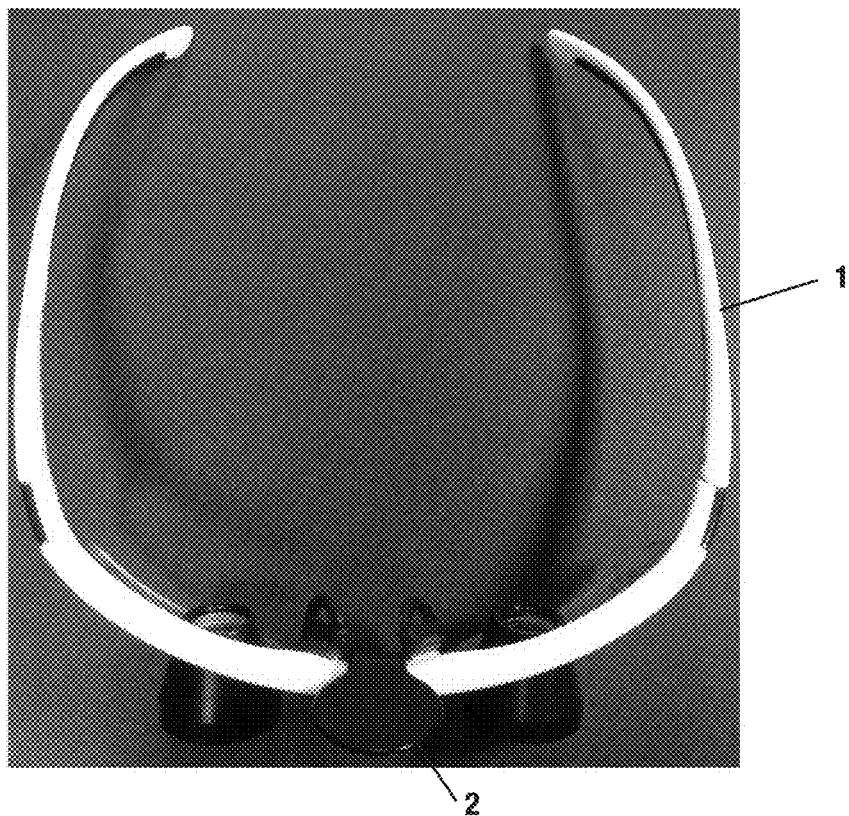
FIG. 3 is a top view of the loupe with the mount
Figure 4:
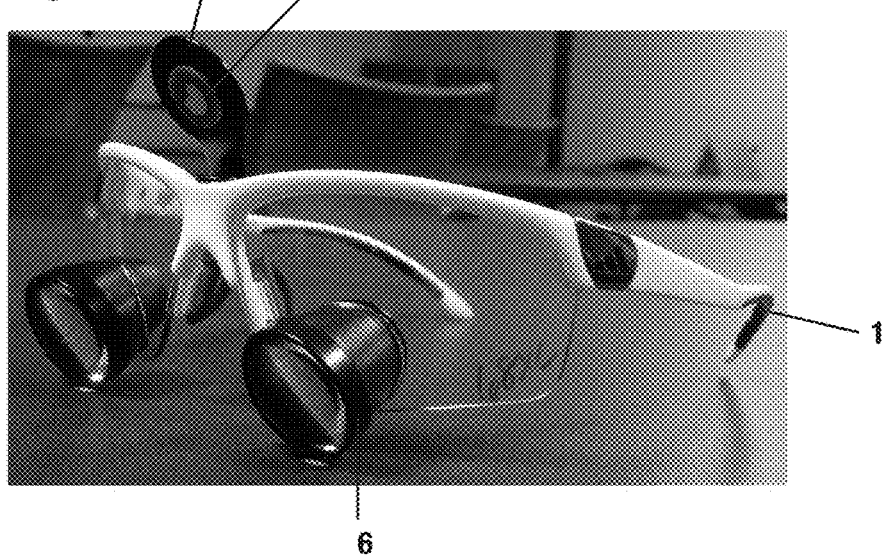
FIG. 4 is a perspective view of the loupe with the mount

FIGS. 2-4 depicts frame 1 without the headlamp 3 mounted on it. Mount 2 is connected to the loupe frame 1 by any means commonly known in the art to connect a headlamp mounts to frames. The mount 2 can either be a universal-style mount designed to accommodate a wide variety of frames, or it can be a mount specifically designed for a particular frame. The mount 2 also will contain metal component 5. Metal component 5 can be constructed of any number of metals, which magnetic materials are attracted to and can be in any desired shape or configuration. Metal component 5 can be a single piece of metal or it can be a multiple pieces of metal. Metal component 5 may be exposed or it may be embedded within mount 2. The purpose of metal component 5 is to have some metal contained within mount 2 which is attracted to magnetic fields, so that the magnet 10 in headlamp 3 will secure headlamp 3 to mount 2. If frame 1 is a pair of loupes, it will also contain a pair of loupe barrels 6. FIG. 2 depicts the loupe barrels 6 as being of the through the lens (TTL) type, however, the loupe barrels 6 can be of any style of loupes, including, flip-ups.

Figure 41A:
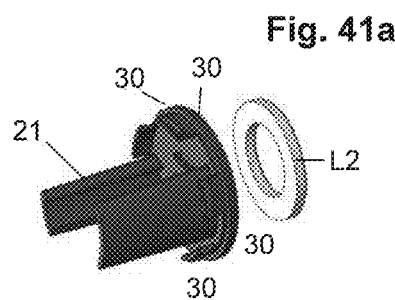
FIG. 41a is an exploded view of the end cap assembly
Figure 41B:
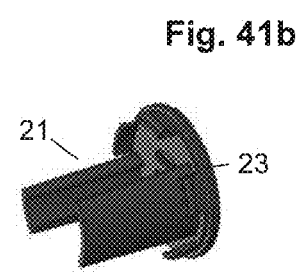
FIG. 41b is an isometric view of the end cap assembly

Headlamp 3 is attached to mount 2 via a magnet 10 located within headlamp 3 as illustrated in FIG. 41a. The magnetic source can be any type of magnetic source such as: rare earth magnets, ferromagnets or electromagnets. In an alternative embodiment, the locations of magnet 10 and metal component 5 can be swapped, so that metal component 5 is located on headlamp 3 and magnet 10 is located on mount 2.

While the preferred embodiment illustrates the use of a magnet as a mechanism to mount the headlamp to the mount, those skilled in the art can adapt any number of attachment mechanisms to attaching the headlamp to the mount. For example, a bayonet mount where the pins are located on the headlamp and fit into slots located on the mount. Other possible mounts includes clips, retaining rings, hook and loop fasteners, and any other attachments which one skilled in the art could adapt to mount the headlamp onto the mount.

Figure 5:
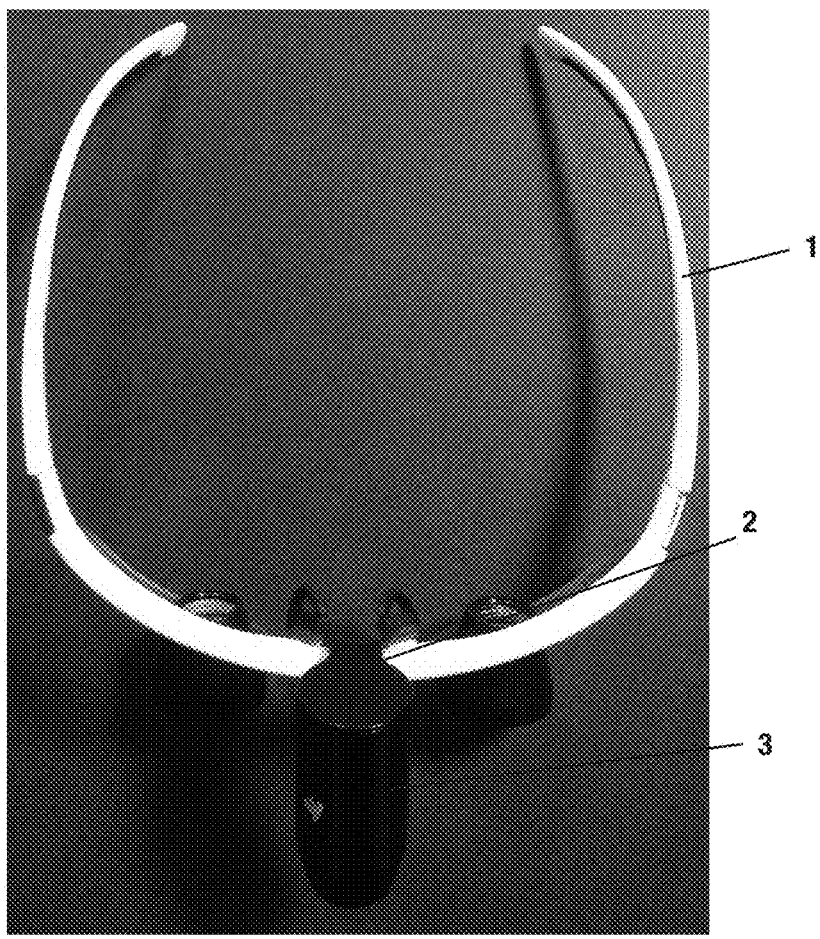
FIG. 5 is a top view of the loupe with the housing
Figure 6:
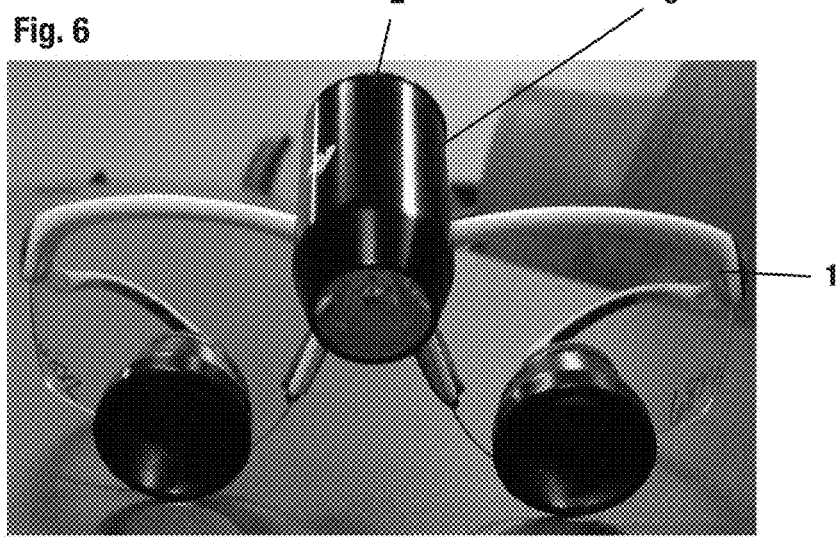
FIG. 6 is a front view of the loupe with the housing
Figure 7:
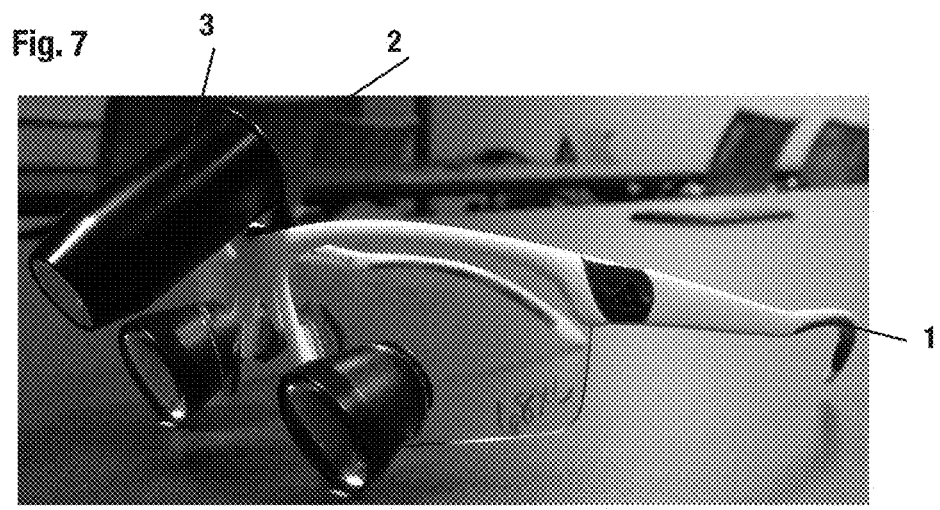
FIG. 7 is a perspective view of the loupe with the housing
Figure 8:
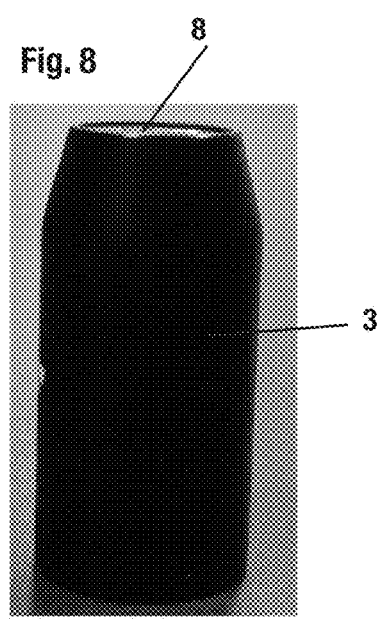
FIG. 8 is a side view of the housing

FIGS. 5-7 depicts frame 1, but with the headlamp 3 connected to the mount 2, which is attached to frame 1. The magnet should be sufficiently strong enough to hold headlamp 3 to mount 2 such that headlamp 3 will not fall off mount 2 during normal use. However, magnet should not be too strong such that headlamp 3 cannot be removed from mount 2.

In order to operate the device, the user needs only to place the headlamp 3 onto mount 2. Only when headlamp 3 is mounted onto mount 2, the light source 9 can be activated in any number of ways. For example, the mere act of placing headlamp 3 onto mount 2 could activate light source 9, while removing headlamp 3 from mount 2 would deactivate light source 9. Other options for light activation includes can be: a disposable sleeve which acts as both a asepsis solution as well as a light activation solution (e.g. placement of the disposable sleeve onto headlamp 3 also activates light source 9), a motion sensor (e.g. when a user waves their hand in front of the motion sensor it activates or deactivates light source 9), twisting headlamp 3, a switch or knob, wireless means (e.g. IR, radio or Bluetooth), a moment circuit, or any other means known in the art to activate and deactivate a light source.

Figure 9:
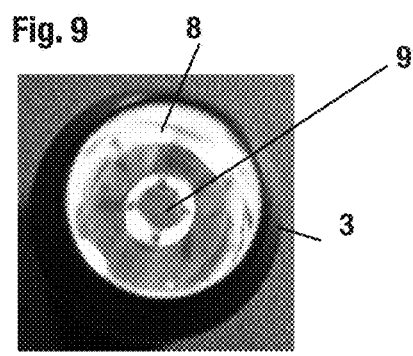
FIG. 9 is a top view of the housing
Figure 10:
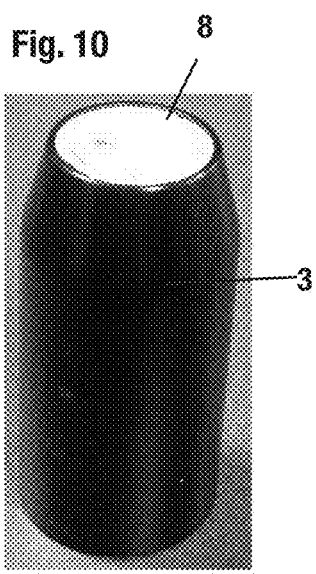
FIG. 10 is a perspective view of the housing
Figure 11:
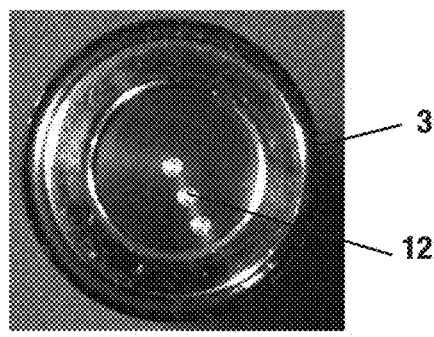
FIG. 11 is a bottom view of the housing

FIGS. 9-11 depicts headlamp 3. Headlamp 3 consists of the housing 7 that houses all of the internal components. Battery contacts 12 are located on the exterior of the housing. Battery contacts 12 functions to provide an electrical connection to mount 2 and to charger 4. The electrical connection between headlamp 3 and mount 2 could facilitate certain functions of headlamp 3 while the electrical connection between headlamp 3 and charger 4 charges battery 24.

Light source 9 can be of the type that emits a single wavelength, a range of wavelengths or multiple discrete wavelengths.

While light source 9 can be any type of light source with the size and illumination properties that meets the desired lighting specifications, light emitting diodes (LEDs) are the preferred light source. LEDs are the preferred light source because of their combination of size, low power consumption, reliability, efficiency, durability and brightness.

The desired luminance output from light source 9 will be in the range of 0-100,000 Lux, with a preferred range of 25,000-30,000 Lux. As discussed in the foregoing, medical and dental professionals prefer to have a light output be as a circular shaped spot. The dimensions of such a circular shaped spot would be approximately 2-15 cm in circumference, with a preferred circumference of about 7 cm. While circular shaped spots are preferred for medical and dental applications of headlamp 3, the headlamp 3 as described herein should not be construed as to being limited to circular shaped spots. For example, oval shaped spots are possible, with the dimensions of this oval spot be from approximately 1.5×2 cm, up to 10×15 cm with a preferred size of about 5×7 cm. However, any other shapes are possible with the only limitations being the ability to shape the light output.

The size of the spot is partially dependent on the distance of focus. Distance of focus is the distance between the lens and point it is concentrated on. The preferred embodiment contemplates a distance of focus of 5"-40", preferably at a range of 14"-26". However, this device could accommodate any desirable distance of focus depending on the users' preference and intended use of the device. The only limitation for the distance of focus would be the currents state of the art of optical technology.

Similarly, color temperature and wavelength could vary according to the user's preference of intended application of the light. In the preferred embodiment, a color temperature of about 6300 Kelvin and white light are desired. However, this device could accommodate any desirable color temperature. While white light is mixture of all colors of visible spectrum, this device could accommodate more specific wavelengths. The only limitation for the color temperature and wavelength are the current state of the art for available light sources.

While the headlamp 3 is depicted as being generally cylindrical in shape, any shape can be used, provided that the internal volume of the headlamp 3 is sufficient to contain all of internal components. Preferably, headlamp 3 will be constructed of aluminum because of its advantageous heat dissipation properties. However, headlamp 3 can be made of any suitable material, such as carbon fiber, other metals (e.g. titanium, stainless steel), plastics, composites or any other materials that have the desired weight, durability and heat dissipation characteristics. The method of manufacturing headlamp 3 can be of any known method of manufacturing such materials, for example, casting or machining If the headlamp 3 is intended to be used for medical, dental or surgical purposes, the material should be sufficient durable and resilient to withstand the additional cleaning requirements inherent with such devices, such as the use of potentially caustic cleaning chemicals, autoclaving or ultrasonic cleaning. Alternatively, disposable asepsis housing sleeves specifically fitted for headlamp 3 can be used.

The device can incorporate multiple headlamps 3, either as spares or for different lighting characteristics. For example, a range of headlamps 3 could be available, with each headlamp having a different run time, wavelength, color temperature or brightness. Headlamps can also have colors or designs for cosmetic purposes.

FIGS. 41a-46b depicts the various component subassemblies that are housed within headlamp 3.

FIG. 41a depicts the individual components that make up end cap assembly 23. End cap assembly 23 consists of end cap 21 and magnet 10, which is affixed to the exterior of end cap 21. Battery contacts 12 will also be found on the end cap 21 as depicted in FIG. 11. In an alternative embodiment, magnet 10 can be affixed to the interior of the end cap 21. In yet another embodiment, end cap assembly may consist of end cap 21 and metal component 5, with magnet 10 affixed to mount 2. End cap 21 can be constructed from any material that is sufficient rigid and durable, such as plastics, metals or carbon fiber.

Figure 42A:
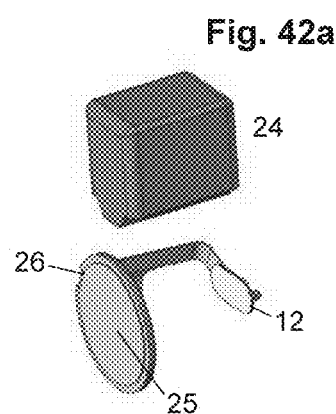
FIG. 42a is an exploded view of the battery assembly
Figure 42B:
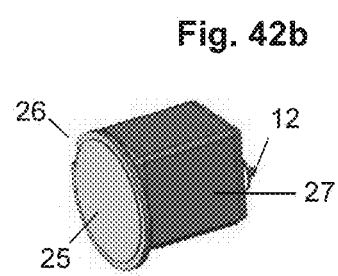
FIG. 42b is an isometric view of the battery assembly

FIGS. 42a-42b depicts the individual components that make up battery assembly 27. Battery assembly 27 is comprised of battery 24, control circuitry 25 and heat sink 26. Battery 24 will be electrically connected to battery contacts 12 to enable a connection to charger contacts 11 located on charger 4 so that battery 24 can be charged. Control circuitry 25 controls at least some of the headlamp 3 functions, such as on/off, dimming, etc . . . Heat sink 26 dissipates heat generated by internal components, such as the light source 9 and battery 24. In the illustrated embodiment, heat sink 26 consists of a gold disc, however, it can consist of any known heat sink technology, such as fans, liquid cooling, phase change materials, heat dissipating metals, etc . . .

Alternatively, control circuitry 25 can be located in mount 2 instead of part of battery assembly 27. In yet another embodiment, control circuitry 25 can be located in both mount 2 and part of battery assembly 27. For example, mount 2 can contain a series of pins, and light intensity can change depending on which pins are engaged by the headlamp 3.

Figure 43A:
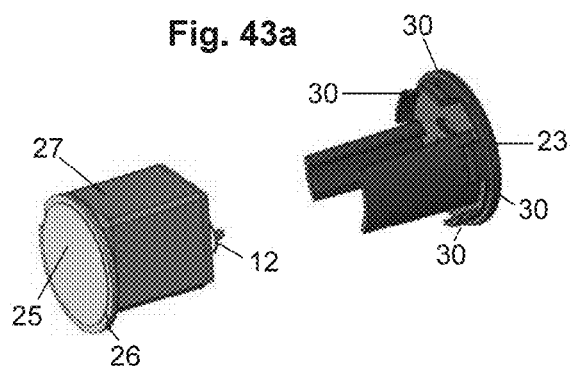
FIG. 43a is an exploded view of the light pod subassembly
Figure 43B:
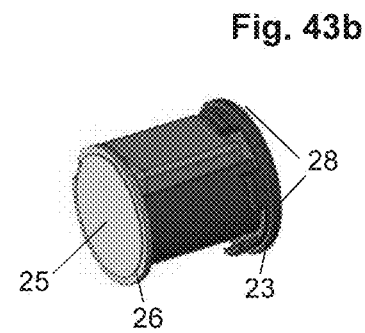
FIG. 43b is an isometric view of the light pod assembly

FIG. 43a depicts an exploded view of the light pod subassembly 28, while FIG. 43b shows a completed light pod subassembly 28. Light pod subassembly is comprised of the battery assembly 27 combined with end cap assembly 23.

FIG. 44a is an exploded view of headlamp 3 which depict the light pod subassembly 28 and housing 7. As the arrow illustrates, light pod subassembly 28 is located within one end of housing 7. FIG. 44b depicts headlamp 3 where light pod subassembly 27 inserted and secured within housing 7. Light pod subassembly can be secured to housing 7 in any number of ways. In the embodiment depicted by FIGS. 44a-44b, end cap 21 features a plurality of tabs 30 which engage corresponding retention features within the housing 7 to secure end cap 21 in place. However, other means are possible, such as adhesives, screws, friction fit or threading, with the only requirement being that end cap 21 should be secured such that end cap 21 is retained within housing 7 when headlamp 3 is removed from mount 2.

FIG. 45a is an exploded view showing that the lens 8 is located at the opposite end of housing 7 from where light pod subassembly 28 is inserted into housing 7. FIG. 45b depicts the lens 8 as mounted within housing 7. FIG. 46a is an exploded view of headlamp 3 showing an O-ring 29 that is used to secure lens 8 in place. FIG. 46b shows headlamp 3 with all components in place. While an O-ring 29 is depicted in this embodiment as the means to secure the lens in place, any other conventional means can be used to secure the lens in place, such as adhesives, retention features (e.g. lugs or ribs), threaded caps, friction fit, etc . . .

Figure 12:
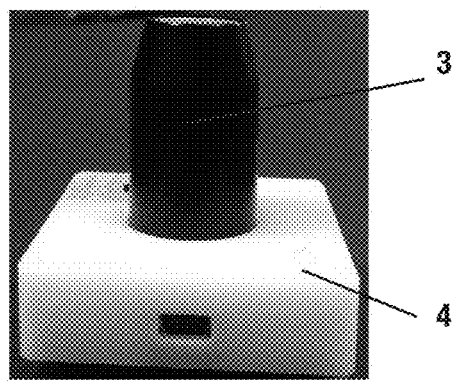
FIG. 12 is a side view of the housing and the charger
Figure 13:
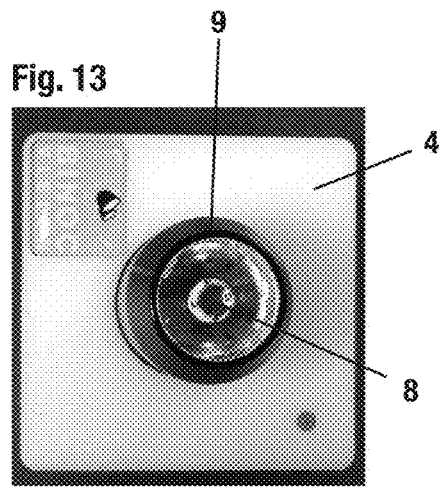
FIG. 13 is a top view of the housing and the charger
Figure 14:
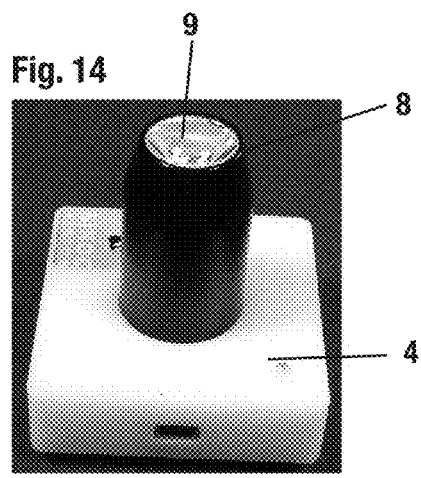
FIG. 14 is a perspective view of the housing and the charger
Figure 15:
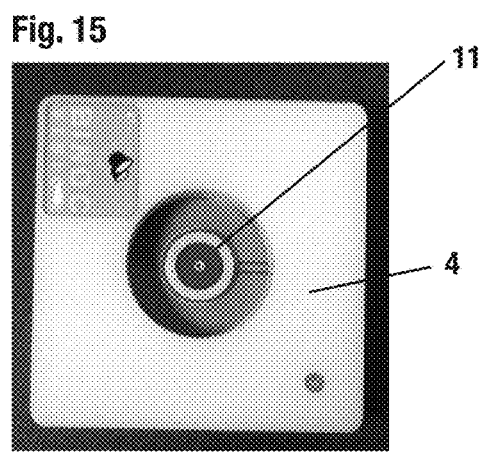
FIG. 15 is a top view of the charger
Figure 16:
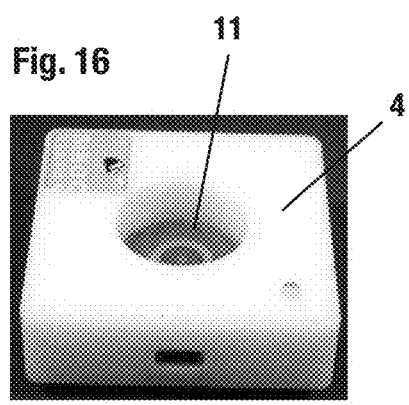
FIG. 16 is a perspective view of the charger
Figure 17:
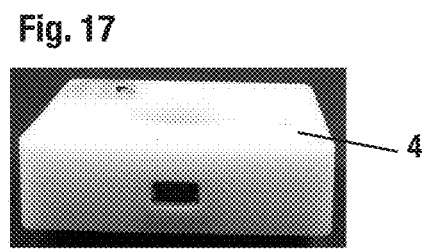
FIG. 17 is a side view of the charger FIG. 18 side view of the through-hole style assembly FIG. 19 exploded view of the through-hole style assembly FIG. 20 isometric view of the through-hole style assembly FIG. 21 side view of the surface mount style assembly FIG. 22 exploded view of the through-hole style assembly FIG. 23 side view of the pocket style assembly FIG. 24 exploded view of the pocket style assembly FIG. 25 side view of the integrated heat sink style assembly FIG. 26 exploded view of the integrated heat sink style assembly FIG. 27 isometric view of surface mount style assembly FIG. 28 isometric view of the integrated heat sink style FIG. 29 isometric view of the pocket style assembly

FIGS. 12-14 depicts headlamp 3 on charger 4, while FIGS. 15-17 depicts the charger 4 by itself. Charger 4 contains the components to charge the battery 24 located within headlamp 3. Such components include charger contacts 11. When headlamp 3 is placed on charger 4, battery contacts 12 creates an electrical connection with charger contacts 11 allowing the battery 24 located in housing 7 to be charged. So when the headlamp 3 is not in use, it can be placed on charger 4, to ensure that the user will always have a charged battery.

An alternative embodiment to the charging system would be the use of an inductive charging system. However, in an inductive charging system, housing 7 could omit battery contacts 12 and charger 4 does not have charger contacts 11 since inductive charging is a non-contact charging, thus, battery contacts 12 and charger contacts 11 would not be needed.

As discussed in the foregoing, LEDs are the preferred light source 9 because of their combination of desirable properties. However, LEDs typically output light in a square shape, not in the round shape that is desired by medical and dental professionals. In order to shape the light output of LEDs from a square shape to a round shape requires additional optical elements, such as multi-optics groups consisting of aspheric elements or reflectors. The addition of such optical elements adds considerable weight and bulk to the light source.

In a device such as the one described herein, weight and size are at a premium. Size is at a premium so that the device remains unobtrusive to the users while it is in use. The combination of weight and size is important so that the certain of gravity is such that it does not fall off and to reduce the fatigue of wearing the device for hours at a time.

A novel way of accomplishing the goals of having a circular spot without the additional optical elements to shape the spot is to incorporate a masking element for the LED. While the masking element was developed in conjunction with LEDs, one skilled in the art would know to adapt this technology to work with any type of light source. The advantages of the inclusion of an LED mask over conventional methods of shaping light outputs can include lower costs, lower weight, decreased design complexity, smaller overall assemblies, reduced manufacturing costs and higher reliability.

A conventional LED assembly would typically consist of a substrate [e.g. a printed circuit board (PCB) or a metal-core printed circuit board (MCPCB)], at least one LED mounted on the substrate, optical elements and any other associated components. In the preferred embodiment of this invention, the control circuitry 25 can act as the substrate. The assembly is mounted within a housing. Above the LED is typically, but not always, at least one optical element such as lenses, reflectors, light pipes, and the like.

The use of a mask introduces an additional element to the conventional LED assembly. In this modified assembly, there is the substrate, at least on LED, optical elements, there is a additional element, the LED mask. The LED mask will be mounted immediately above the LED, so that it is between the LED and the optical element. This LED mask is a separate element from the optical element.

As demonstrated by the following embodiments, the LED mask can be mounted on the substrate with any type of structural support assembly such that it is located immediately above the LED. It can be mounted by any number of conventional methods, such as, but not limited to soldering by using surface-mount (SMT) techniques, through-hole techniques, or wire-bond (welding) techniques. The LED mask can also be mounted directly to a LED with a sub-mount assembly.

The LED mask can be made of any material that has a non-reflective surface, such as, but not limited to metals, plastics and composites. The LED mask will have a hole that is aligned with the LED. Typically, the hole will be round in shape with a diameter of about 0.1 mm to 2 mm, or any diameter that is roughly tied to up to 100% of the LED's emission surface. While the shape of the hole will typically be a circle, any other shape and size that is desired can be used, such as, but not limited to: triangles, squares, rectangles, ellipses, polygons, and the like. In addition, the hole can be also be a symbol. The LED mask with a shape or symbol has the primary advantage of preventing stray light from being emitted from the LED. This can improve the effectiveness of the other optical elements in the system and eliminate common light abnormalities that have a detrimental effect on the performance of lighting systems, such as halos, rings, stray light and other abnormalities.

Figure 18:
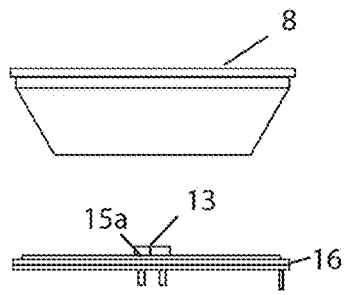
Figure 19:
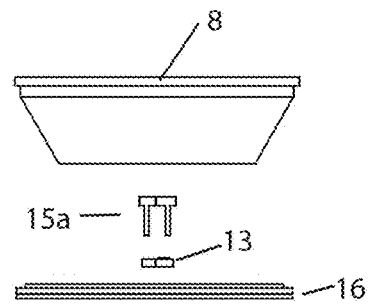
Figure 20:
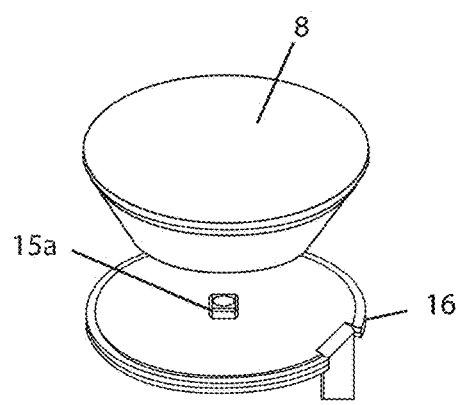

FIGS. 18, 19, 20, 31a, 31b and 31c depict an embodiment of the present invention where the LED mask 15 is mounted to the substrate by way of a through-hole style of mounting. The LED mask 15 contains a hole 18 for light emitted from the LED 13 to pass through to reach the lens 8. FIGS. 18 and 20 depict the lens 8 mounted above the substrate 16, where the LED mask 15 and LED 13 are mounted. FIG. 19 is an exploded view, which depicts the lens 8, LED mask 15, LED 13 and the substrate 16. FIGS. 31a-31c depict various angles of the LED mask 15a itself. As seen in FIGS. 14a-14c, the LED mask contains a plurality of legs 17 that pass through corresponding through-holes on the substrate 16. The legs 17 are then affixed to the substrate 16 by any known method associated with through-hole mounting, such as friction (press-fit), adhesive, soldering, forming/bending, or the like, which effectively mounts the LED mask 15 to the substrate 16.

Figure 21:
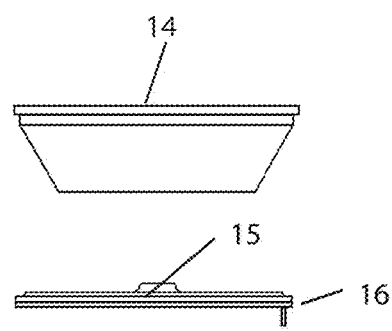
Figure 22:
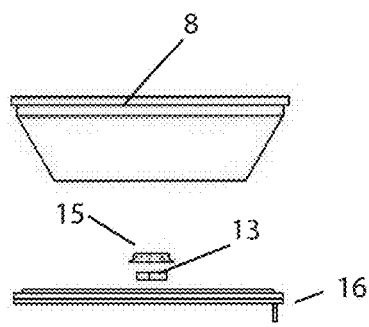
Figure 27:
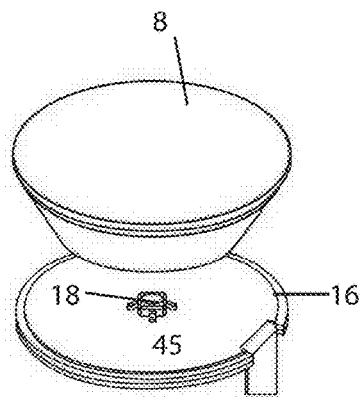

FIGS. 21, 22, 27, 32a, 32b and 32cc depict an alternative mounting style of the present invention where the LED mask is mounted on the surface of the substrate by way of surface mount technique. FIGS. 21 and 27 depicts the lens 8 mounted above the substrate, but the LED mask 15 is mounted on the substrate by way of solder, adhesive or any other known surface mounting techniques. FIG. 22 is an exploded view, which depicts the lens 8, LED mask 15, LED 13 and the substrate 16. LED mask 15 contains a plurality of tabs 19 which are used to mount the LED mask 15 to substrate 16. FIGS. 32a-32c depict various angles of the LED mask 15 itself, along with tabs 19.

Figure 23:
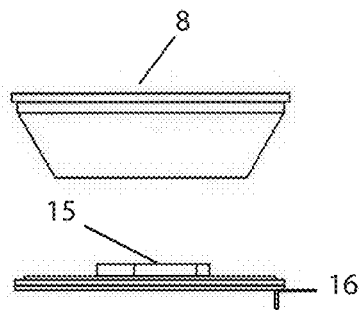
Figure 24:
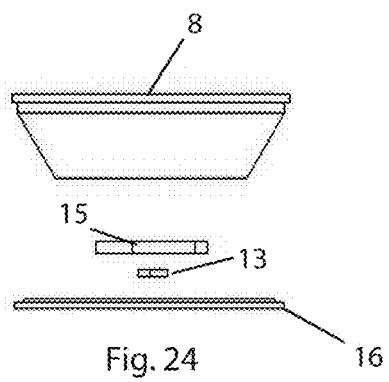
Figure 29:
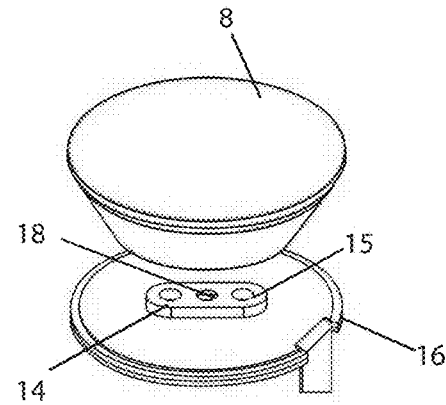

FIGS. 23, 24, 29, 33a, 33b and 33c depict another alternative embodiment of the present invention where the LED mask 15 is manufactured from a single piece of material with a plurality of mounting points 14. The method of manufacture can be any known method of manufacturing such parts, such as, but not limited to, machining, milling, forming or molding. The mounting points 14 are the areas on the LED mask 15 where mounting hardware interfaces with the LED mask 15 and the substrate 16 to mount the LED mask 15 onto substrate 16. The mounting hardware can be any conventional type of mounting hardware, such as screws, clips or pushpins. FIGS. 23 and 29 depict the lens 8 mounted above the substrate 16, but the LED mask 15 is mounted on the substrate 16 by way of mounting hardware with the mounting points 14. FIG. 24 is an exploded view, which depicts the lens 8, LED mask 15, LED 13 and the substrate 16. FIGS. 33a-33c depict various angles of the LED mask 15, along with the hole 18 and mounting points 14. In this particular embodiment, the mounting points consist of a pair of depressions, or pockets, with screw holes. The LED mask 15 is then secured to the substrate 16 by screws.

FIGS. 34a, 34b and 34c depict an alternate embodiment of the LED mask 15 that is mounted to the substrate 16 by way of mounting points 14 and mounting hardware. However, in this embodiment, the LED mask 15 is not made from a single piece of material. As illustrated, this embodiment depicts the LED mask 15 made from multiple components—specifically, two layers. However, the LED mask 15 can be made by any number of components arranged in any number of ways and is not limited to two layers. This approach would be advantages if the LED mask 15 were constructed from multiple materials and components.

Figure 25:
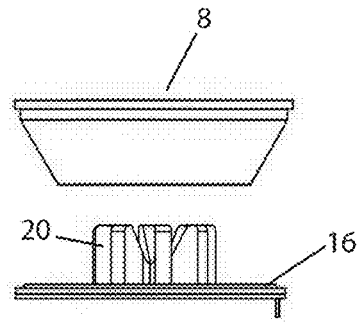
Figure 26:
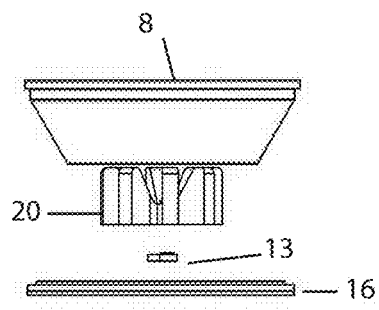
Figure 28:
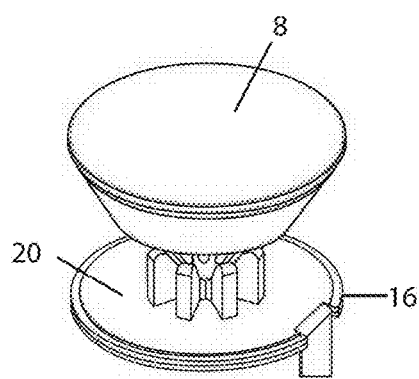

FIGS. 25, 26, 28, 30a, 30b and 30c depict another alternative embodiment where the LED mask is integrated with a heat sink 20. Possible heat dissipation elements include construction from materials known to dissipate heat, such as, but not limited to, copper and aluminum. In the alternative, the LED mask 20 can have heat dissipation features, such as heat pipes, cooling fins or hollowed areas filled with heat dissipating materials, for example, phase change materials. The heat sink integrated with the LED mask 20 can be mounted to the substrate 16 by any suitable method, such as, but not limited to what is described herein. FIGS. 25 and 28 depicts the lens 8 is mounted above the heat sink integrated LED mask 20. FIG. 26 is an exploded view, which depicts the lens 8, heat sink integrated LED mask 20, LED 13 and substrate 16. FIGS. 30a, 30b and 30c are various angles of the heat sink integrated LED mask 20 with hole 18.

Other embodiments include incorporating the LED mask 15 into the optical element, for example integrating the LED mask 15 with the lens 8. In yet another embodiment, the LED mask 15 is incorporated as part of the LED 13.

Initially, the purpose of incorporating the LED mask was to incorporate a cost effective way of changing the shape of the light that is projected from the LED. Also, the small form factor of the LED mask versus the optical elements of traditional methods made it particularly advantageous for small form-factor illumination devices, particularly ones where only a single LED source is used. However, the LED mask can be adapted to illumination devices where multiple LED sources are used.

However, an unexpected effect of incorporating this LED mask with LED is that not only was it a cost effective way of changing the shape of the light projected from the LED, it also improved the light output qualities of the LED. Some of these light output qualities includes: cleaner, more defined spot of light with edges that are sharper, or have more contrast than the surface that the light is projected on.

As an illustration of the measureable advantages that the LED mask presents over not having the LED mask, two test runs were performed: Test Run AB and Test Run AC. An examination of Tables 1 below shows that the parameters of Test Run AB and Test Run AC are identical (identical LEDs, same drive current, same lens specifications, same distance, etc . . . ), with the only difference being the presence of the LED Mask in Test Run AB and the absence of the LED Mask 15 in Test Run AC. These test runs compared the use of LED mask against not using LED mask in achieving a circular spot with a diameter of 65 mm at a distance of 350 mm from the optic exit face.

TABLE 1

| Iteration | Run AB | Run AC |
| --- | --- | --- |
| LED | Lumileds Luxeon Z ES LXZ2-5790-y | Lumileds Luxeon Z ES LXZ2-5790-y |
| Nominal CCT | 5700k | 5700k |
| Min CRI | 90 | 90 |
| Drive Current | 350 mA | 350 mA |
| Assumed Junction Temperature | 85° C. | 85° C. |
| Assumed LED Output | 105 lm | 105 lm |
| Lens Material | Polycarbonate (n = 1.586) | Polycarbonate (n = 1.586) |
| Housing/PCB Material | Semi-gloss black | Semi-gloss black |
| Cover Lens | None | None |
| LED Mask | 0.2 mm think, 1.6 mm dia. Opening | None |
| Design Style | Entrance Shaft Collimator, axially symmetric, LED Mask | Entrance Shaft Collimator, axially symmetric |
| Lens Diameter (Optical) | 23.1 mm | 23.1 mm |
| Lens Diameter (Total) | 25.5 mm | 25.5 mm |
| Lens Height (exit surface) from PCB | 15.0 mm | 15.0 mm |
| Fillet Radius | 0.1 mm | 0.1 mm |
| Outer Lip Thickness | 1.6 mm (thickness added towards LED) | 1.6 mm (thickness added towards LED) |
| % Emitted Light Falling Within 65 mm Dia. (350 mm from optic exit face) | 90% | 87% |

Figure 35A:
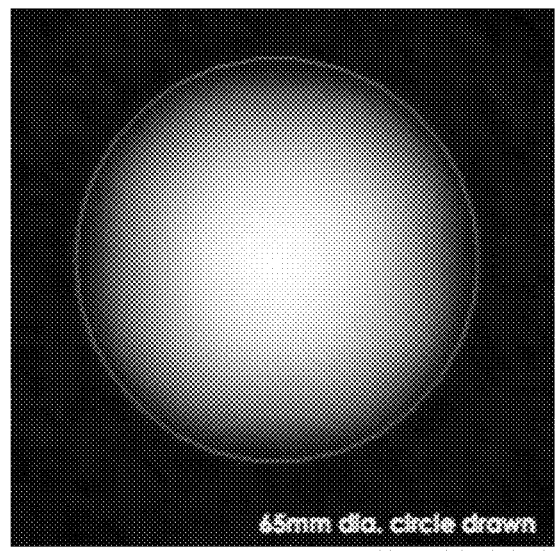
FIG. 35a is a view of the spot after passing through the LED mask
Figure 35B:
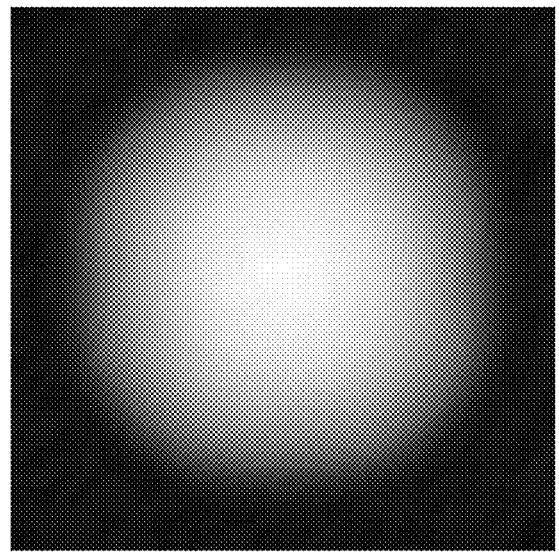
FIG. 35b is a view of the spot after passing through the LED mask

FIGS. 35a-35b are from Test Run AB, and it depicts that with the LED mask, the shape of the spot in test run 1 is easily shown to be circular, which, as stated in the foregoing is the desired shape for Test Run AB. FIG. 35a has a 65 mm diameter circle superimposed on the light to illustrate the desired diameter that was being sought in Test Run AB, and as a visual cue as to how the closely shape of the actual spot compares relative to the desired circular shape. FIG. 35b is the same image, just without the 65 mm diameter circle superimposed onto the figure.

Figure 36A:
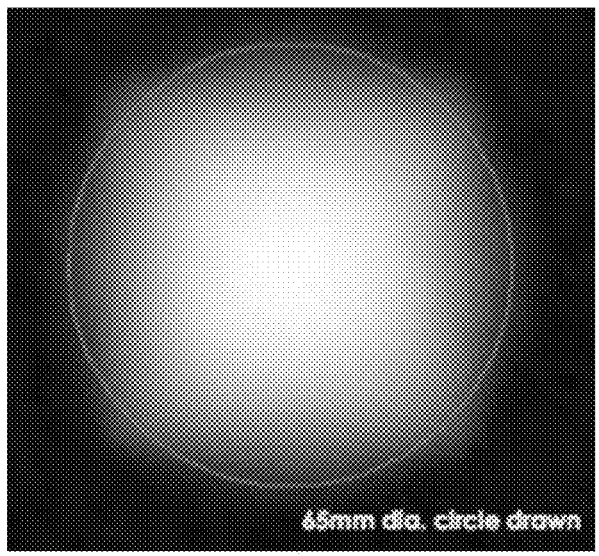
FIG. 36a is a view of the spot without passing through the LED mask
Figure 36B:
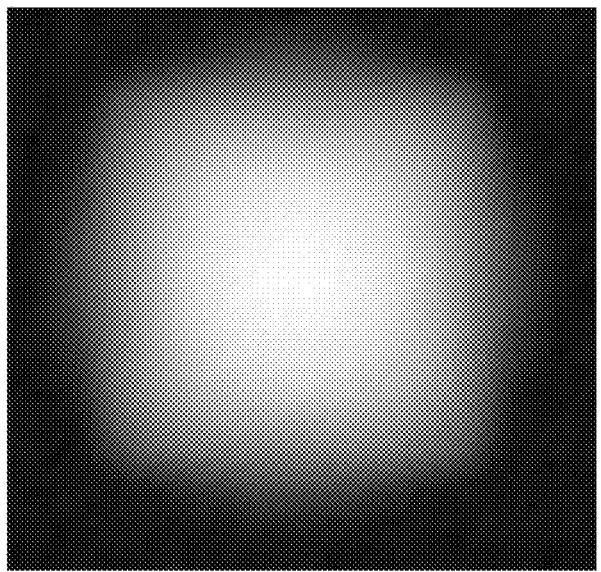
FIG. 36b is a view of the spot without passing through the LED mask

Similarly, FIGS. 36a-36b are from Test Run AC. With these figures, it clearly demonstrates that the shape of the spot generated in Test Run AC is not circular in nature. Rather, the shape is more akin to a square shape, but with rounded sides. FIG. 36a depicts the spot generated in Test Run AC with the 65 mm diameter circle superimposed as a visual cue for the desired 65 mm diameter spot that was sought after in Test Run AC. As FIG. 36a demonstrates, the spot is not circular, and the four corners of the spot extend beyond the superimposed circle. Thus, without the LED mask, the shape of the light is less than desirable and exceeds the desired parameters. FIG. 36b is the same image, but without the superimposed circle. So, a comparison of the images presented in FIGS. 35a-35b and 36a-36b demonstrates that the use of the LED mask results in a spot that is more closely achieves the desired spot shape.

FIG. 37 is a depiction of the exit face contour plot for Test Run AB, which measures the light intensity. Similarly, FIG. 38 is a depiction of the exit face contour plot for Test Run AC. A comparison of FIGS. 37 and 38 confirms that with the LED mask, the light has a clearly defined circular shape, which is once again, the desired shape sought in both Test Run AB and Test Rub AC.

Figure 39A:
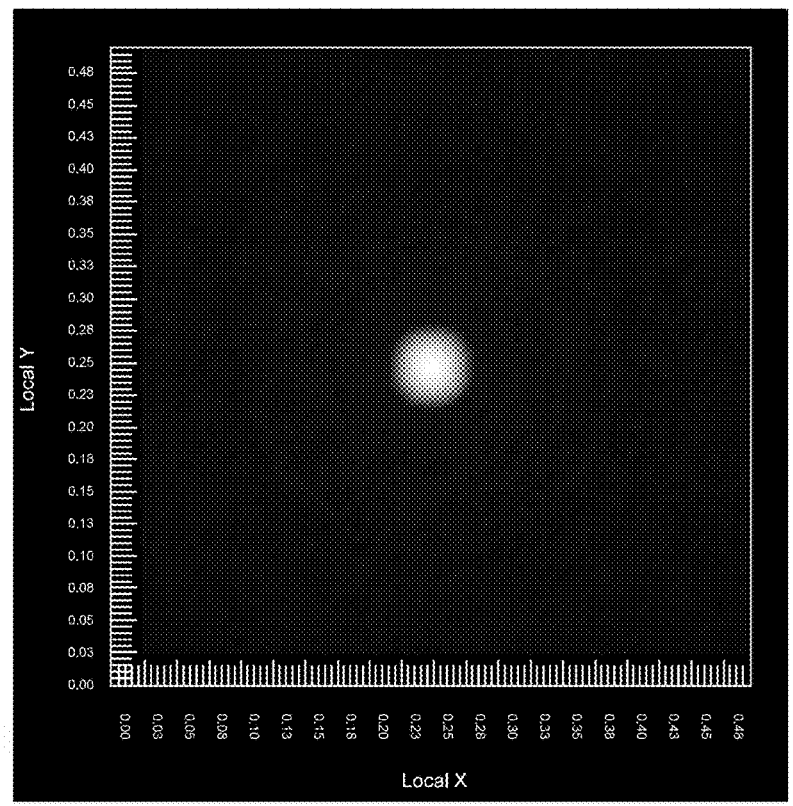
FIG. 39a is a grey shaded plot
Figure 39B:
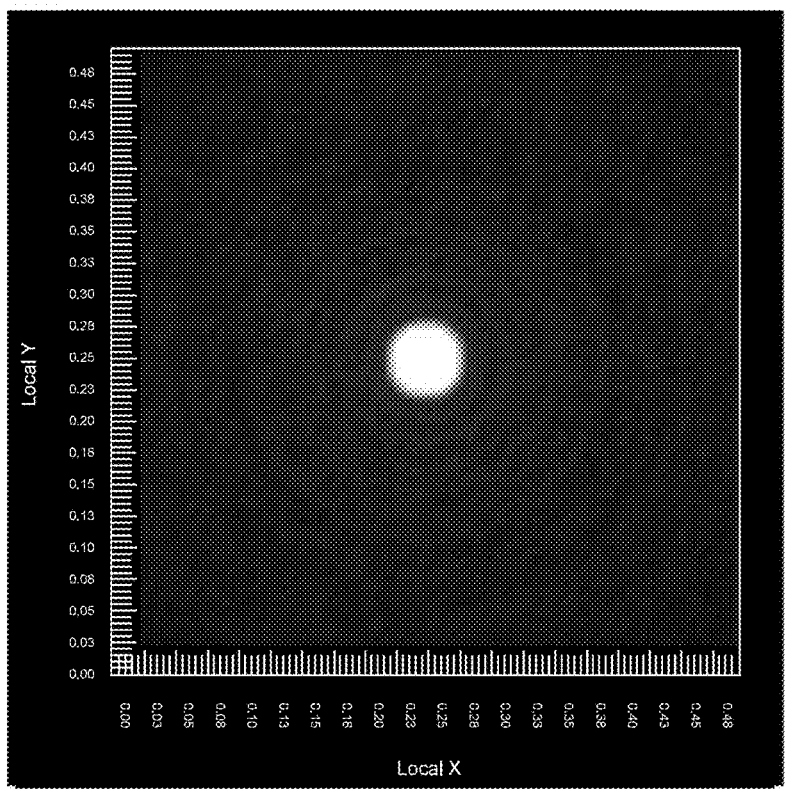
FIG. 39b is an over-exposed grey shaded plot
Figure 40A:
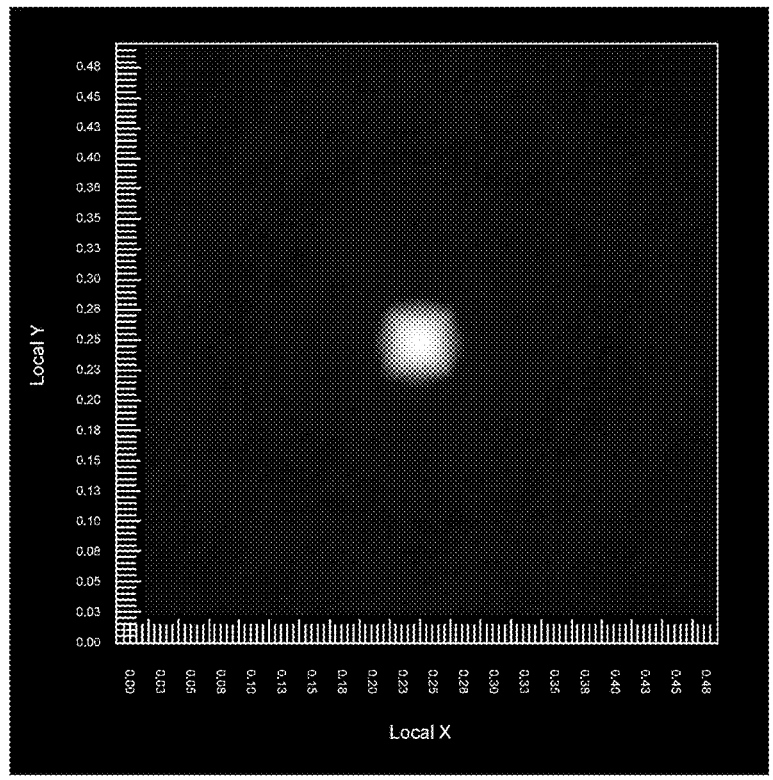
FIG. 40a is a grey shaded plot
Figure 40B:
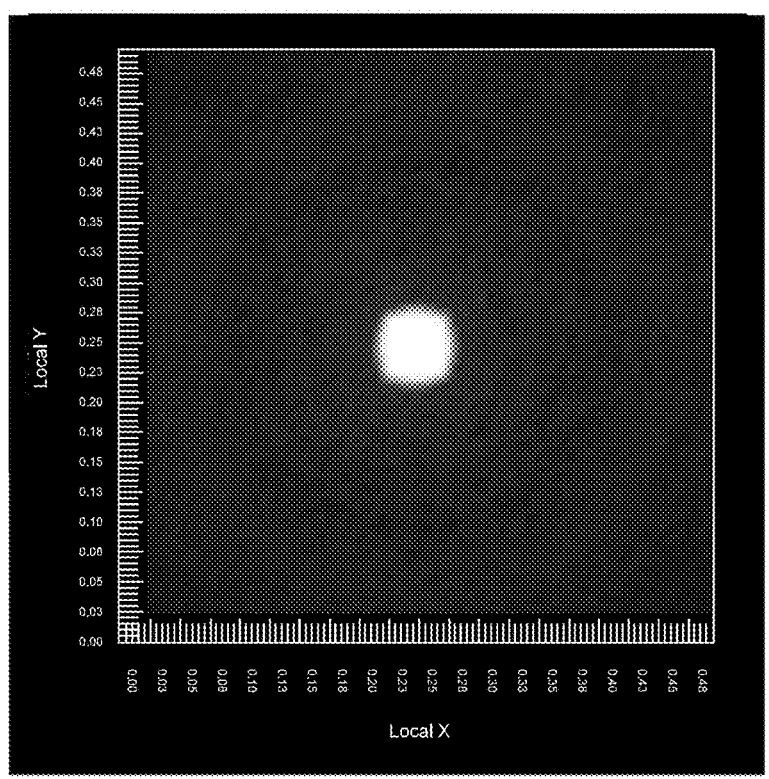
FIG. 40b is an over-exposed grey shaded plot

FIG. 39a is a grey shaded plot that depicts the relatively light intensity, where the light intensity correlates with the greyscale of the image. The more intense the light, the lighter the grey color, whereas the less intense the light, the darker the grey color is. FIG. 39b is the same image, except that the image is over-exposed, so that any luminance over a certain level is white in color. What FIGS. 39a and 39b demonstrate once again, is that the spot with the LED mask has uniform circular shape, which is the ideal shape that Test Run AB was seeking FIGS. 40a and 40b are similar to FIGS. 39a and 39b, except that those figures came from Test Run AC, which is the test run without the LED mask 15. Once again, FIG. 40a is a greyscale image of the light, whereas FIG. 23b is the same image as 40a, except that it is over-exposed. FIGS. 40a and 40b demonstrates that without the LED mask, the spot of light is square shaped, not the circular shape that is desired.

Thus, as demonstrated by the foregoing, usage of the LED mask is an effective method of changing the shape of the light output of LED 13. Furthermore, because the use of the LED mask provides a way to change the shape of the light output of LED without the need for complex optical systems. As a result, the use of LED mask, it is a cost effective method of changing the shape of the light output without affecting peak intensity and improving the output quality of the light. Furthermore, because the use of the LED mask is able to achieve the same results as using complex optical elements, the end result are lower costs, lower weight, decreased design complexity, smaller overall assemblies, reduced manufacturing cost and high reliability relative to convention methods of shaping the output LED.

The foregoing description represents the exemplary embodiments of this invention. It is intended to be descriptive of the invention and not limiting. Those skilled in the art will know that additional modifications, changes and substitutions can be made without deviating from the scope and spirit of the invention.

We claim:

1. A cordless headlamp system comprising:
   a frame worn on a user's head;
   a mount coupled to said frame;
   a metal component attached to said mount, wherein said metal component is comprised of a metal that is attracted to magnetic fields;
   a headlamp comprised of a housing with an internal space, at least one lens, and an end cap;
   said end cap further comprises a magnet coupled to said end cap;
   said internal space of said housing further comprises at least the following components: at least one battery in electrical communication with a control circuit and a light source coupled to said control circuit;
   wherein said magnet located on said end cap generates a magnetic field which attracts said metal component located on said mount and secures said headlamp to said mount.

2. The cordless headlamp system of claim 1 wherein said light source is a light emitting diode.

3. The cordless headlamp system of claim 2 wherein said control circuitry further comprises an LED mask, wherein said LED mask is comprised of a material which is mounted on said control circuit, but above said LED, and a hole aligned with said LED.

4. The cordless headlamp system of claim 1 wherein said headlamp weights approximately 20-40 g.

5. The cordless headlamp system of claim 1 wherein said housing is cylindrical in shape.

6. The cordless headlamp system of claim 1 wherein said control circuitry controls at least one function of said headlamp.

7. The headlamp system of claim 1 wherein said headlamp emits light with a desired luminance in the range of 20,000-90,000 lux.

8. The cordless headlamp system of claim 1 wherein light emitted by said light source has a color temperature of about 6300 Kelvin.

9. The cordless headlamp system of claim 1 wherein said housing is cylindrical in shape.

10. A cordless headlamp system comprising:
a frame worn on a user's head;
a mount coupled to said frame;
a metal component attached to said mount, wherein said metal component is comprised of a metal that is attracted to magnetic fields;
a headlamp comprised of a housing with an internal space, at least one lens, and an end cap;
said end cap further comprises a magnet coupled to said end cap;
said internal space of said housing further comprises at least the following components: a heat sink, at least one battery in electrical communication with a control circuit and a light source coupled to said control circuit;
wherein said magnet located on said end cap generates a magnetic field which attracts said metal component located on said end cap and secures said headlamp to said mount.

11. A cordless headlamp system comprising:
a frame worn on a user's head;
a mount coupled to said frame;
a metal component attached to said mount, wherein said metal component is comprised of a metal that is attracted to magnetic fields;
a headlamp comprised of a housing with an internal space, at least one lens, and an end cap;
said end cap further comprises a magnet coupled to said end cap;
said internal space of said housing further comprises at least the following components: at least one battery in electrical communication with a control circuit and a light source coupled to said control circuit;
said control circuitry further comprises an LED mask, wherein said LED mask is comprised of a material which is mounted on said control circuit, but above said LED, and a hole aligned with said LED, and a heat sink,
wherein said magnet located on said end cap generates a magnetic field which attracts said metal component located on said mount and secures said headlamp to said mount.

12. A cordless headlamp kit comprising:
a frame;
a mount removably coupled to said frame, wherein said mount contains at least one metal component which is attracted to magnetic fields;
a headlamp comprising of a housing, wherein said housing is comprised of an internal space, at least one lens and an end cap;
wherein said internal space further comprises at least one battery in electrical communication with a control circuit, said control circuit coupled to a light source;
wherein said end cap further comprises at least one magnet; and
a charger.

13. The cordless headlamp kit of claim 12 wherein said charger is an inductive charger.

14. A cordless headlamp system comprising:
a frame worn on a user's head;
a mount coupled to said frame;
at least one magnet attached to said mount;
a headlamp comprised of a housing with an internal space, at least one lens, and an end cap;
said end cap further comprises at least one metal component, wherein said metal component is comprised of a metal that is attracted to magnetic fields;
said internal space of said housing further comprises at least the following components: at least one battery in electrical communication with a control circuit and a light source coupled to said control circuit;
wherein said magnet located on said mount generates a magnetic field which attracts said metal component located on said end cap and secures said headlamp to said mount allowing said headlamp to be rotated by a user to activate said headlamp while secured to said mount.

* * * * *